Figure 1:
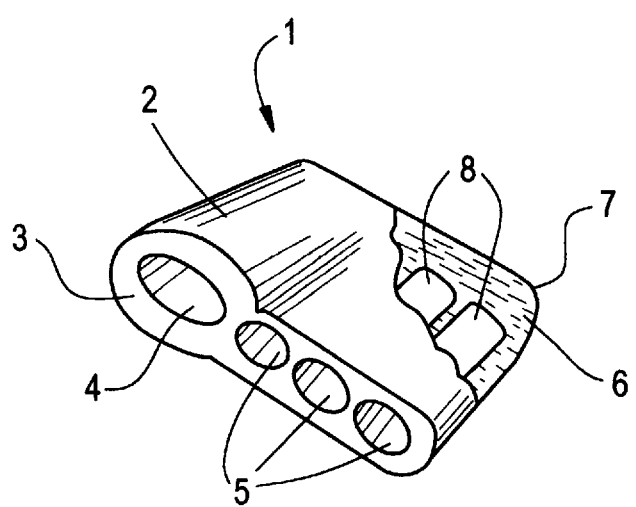

United States Patent

Mosley

[11] Patent Number: 5,879,315
[45] Date of Patent: Mar. 9, 1999

[54] HOT AND COLD DIGIT PACK

[76] Inventor: Keith A. Mosley, 439 Shannon Dr., Atlanta, Ga. 30310

[21] Appl. No.: 617,134

[22] Filed: Mar. 18, 1996

[51] Int. Cl.[6] ........................................... A61F 5/00
[52] U.S. Cl. ................... 602/14; 602/22; 607/111
[58] Field of Search ................ 602/2, 14; 607/96, 607/104, 108, 111, 114; 2/159, 163

[56] References Cited

U.S. PATENT DOCUMENTS

| 543,177 | 7/1895 | Daly | 607/111 |
|---|---|---|---|
| 1,549,510 | 8/1925 | Schnitzler | 607/111 |
| 3,874,000 | 4/1975 | Altman | 607/111 X |
| 4,573,447 | 3/1986 | Thrash et al. | 607/111 X |
| 5,369,807 | 12/1994 | Cho et al. | 2/159 |

*Primary Examiner*—Richard J. Apley
*Assistant Examiner*—Kim M. Lee

[57] ABSTRACT

A hot/cold digit pack is provided having a molded unit with hollow chambers, dimensioned to accommodate a thumb and different sized fingers, and a heat transferring substance encased by the external walls of the molded unit. The unit has a body formed from a durable and resilient plastic material, capable of withstanding heat and cold, and is adapted to be collapsed upon application of slight hand pressure and a face where the openings to the chambers are located.

3 Claims, 1 Drawing Sheet

HOT AND COLD DIGIT PACK

FIELD OF THE INVENTION

This invention relates to a hot/cold digit pack with the primary object of applying, in a manner hereinafter set forth, a novel means of administering heat or cold to injured fingers for the reduction of pain and swelling and to expedite healing. It relates more specifically to a device containing one or more chambers surrounded by a heat transferring gel or liquid composition, into which fingers or a thumb can be inserted.

BACKGROUND OF THE INVENTION

Injuries caused by closing doors, windows and other means are not uncommon to toddlers and young children. An untold number of children have gotten one or more fingers pinched or smashed. Injuries to the fingers are preferably treated by immediately applying pressure to and/or cooling the injured limb. Cooling serves to reduce the flow of blood to the injured area so that subsequent swelling, inflammation, and trauma to the area is minimized. A small child's threshold for pain is practically nonexistent when a finger has been injured so the cooling method not only has to be quick and convenient, but it must have a comfortable touch to the injured part. Adults, like children, also sustain injuries to their fingers and require the same therapeutic consideration. Whereas cold treatment reduces debilitating swelling, heat treatment accentuates the healing process. Other injuries or conditions, such as arthritis, are preferably treated by applying heat to the injured area.

A major difficulty in treating fingers and thumbs lies in concurrently providing hot or cold exposure to all surfaces (top, bottom and sides) of the injured digit. Ice may satisfactorily cool a bodily injury, but it may be sharp, it must be contained in some containment means to prevent leakage, it cannot be reused, and its application is messy and inconvenient.

Alternative means to cool or heat injuries have been devised. U.S. Pat. No. 5,383,921 describes a heat and/or cold device in the form of a muff into which the hands, wrists, arms or legs can be inserted. U.S. Pat. No. 4,592,358 discloses a device featuring a plurality of compartments enclosing a therapeutic substance, that may be heated or cooled, which may be firmly positioned on various body portions using one or more strap means. U.S. Pat. No. 4,951,666 describes a thermal pack consisting of a porous outer bag and a nonporous inner bag for use in treating localized injuries such as the knee. U.S. Pat. No. 5,133,348 discloses a hot or cold pack with a main body portion and four radially extending portions attached thereto and integral therewith which is applied to a curved contour such as breast, knee, ankle, shoulder or other body areas. U.S. Pat. No. 4,530,220 describes a deformable bag comprised of small pieces of gel packed in a flexible envelope for use as a cooling medium which can be applied on different objects or portions having various configurations. U.S. Pat. No. 3,736,769 discloses a cooling device having a core of cold storing material sandwiched between two thin, flexible walls having different heat transfer rates such that the one side of the cooling device is colder to the touch than the opposite side of the device.

The means heretofore available are not efficient and comfortable modes of administering uniform cold/heat to the surface of a injured finger or thumb.

The present invention comprises a molded unit with multiple hollow chambers, in which a thumb and/or fingers can be inserted, and a heat transferring element, that can be heated or cooled, that are encased by the external walls of the molded unit. The entire outer surface of the hollow chambers are immersed in the heat transferring element thereby providing a uniform distribution of hot/cold exposure inside the chambers. The unit will be made of a durable, yet flexible, material that can withstand refrigeration, boiling and/or microwaving.

SUMMARY OF THE INVENTION

In accordance with this invention, a molded unit with hollow chambers dimensioned for a thumb and fingers is provided for administering hot/cold therapy to the injured fingers of toddlers, children and adults. The unit is fabricated from either a rubber, vinyl, plastic or some other flexible material by a molding process. The unit has a wall structure of a thickness such that the chambers may be collapsed with moderate hand pressure to the outer surface of the unit. The openings to the chambers are on the face of the unit. The chambers are dimensioned to provide a loose fit for one thumb and different sized fingers. A heat transferring substance, gel or liquid, and the chambers are encased by the external walls of the molded unit. In accordance with this invention, the chambers are thoroughly immersed in the heat transferring substance, thus producing an even distribution of heat/cold inside the chambers.

These together with other objects and advantages which will become subsequently apparent reside in the details of construction and operation as more fully hereinafter described and claimed, reference being had to the accompanying drawings forming a part hereof, wherein like numerals refer to like parts throughout, and in which:

FIG. 1 is an elevational view of a molded unit with hollow chambers dimensioned for a thumb and different sized fingers.

Referring now to the drawing in detail, it will be seen that the embodiment of the invention which has been illustrated comprises molded unit 1. This molded unit 1 includes a body portion 2 of a rectangular configuration having a face 3 where the openings to a thumb chamber 4 and multiple finger chambers 5 are located. The chambers are not shown in greater detail, but they are molded to the underside of the face 3, have gaps between them, and do not touch the internal wall of the molded unit 1. While the illustrative embodiment of the chambers and molded unit is shown and illustrated as providing clearance for the immersion of the chambers by the heat transferring substance 6, it will be understood that other means of positioning the chambers may be employed.

The molded unit 1 as indicated is formed by a blow molding process from an appropriate type of plastic material. The material that is used is of a type having resilience such that when the wall structure is collapsed and the pressure is removed, the wall structure will return to its original shape. Such a molded unit structure also has a wall 7 of medium thickness throughout the body portion 2. The thumb chamber 4 and fingers chambers 5 are created during the molding process. Other means of forming the molded unit may be employed. The molded unit can be dimensioned for toddlers, children, adults and athletes.

The heat transferring substance 6 will occupy the vacant space around the external chamber walls 8. The substance can either be a gel or a liquid and can be inserted and sealed into the molded unit during the molding process.

It is thought that the operation of the illustrative embodiments will be readily apparent from a consideration of the foregoing. Briefly, the molded unit 1 is either refrigerated or heated before use. The injured digit is inserted into one or more of the chambers 4 or 5. If compression to the injured area is desired, applying pressure to the external wall 7 will cause the inner walls of chambers 4 and 5 to converge.

The foregoing is considered as illustrative only of the principles of the invention. Further, since numerous modifications and changes will readily occur to those skilled in the art, it is not desired to limit the invention to the exact construction, number of chambers, geometric shape and operation shown and described, and accordingly all suitable modification and equivalents may be resorted to, falling within the scope of the invention as claimed.

What is claimed as new is as follows:

1. A thermal therapy hot or cold digit pack adapted to receive the thumb and fingers of a user for administering thermal therapy to injured thumb and fingers, comprising:

a molded unit having a body portion including an external chamber wall, an internal chamber wall and a heat transferring substance enclosed therebetween, said body portion further including opposite face ends, one of said opposite face ends having a plurality of hollow chambers defining finger receiving openings, said hollow chambers having an external surface attached to an underside of said face end and positioned to allow the entire external surface of said chambers to be thoroughly immersed in said heat transferring substance, each hollow chamber adapted to receive only a single finger or thumb such that only the fingers and thumb are inserted into the hollow chambers receive thermal therapy, said body portion having a predetermined thickness and being constructed from a flexible material which enables said body portion to have the characteristic of resilience to thereby allow said body portion to return to its original shape once a collapsing force has been applied and then removed, said body portion being further able to withstand refrigeration and heating, and said hollow chambers adapted to converge when a collapsing force is applied to the external surface of the molded body portion.

2. A molded unit with hollow chambers according to claim 1 wherein the heat transferring substance can either be a gel or liquid capable of being heated or chilled, and covers the entire external surface area of the chambers.

3. A molded unit with hollow chambers according to claim 1 wherein openings to the chambers are located in the face of the unit.

* * * * *